United States Patent
Hong et al.

(10) Patent No.: US 11,659,999 B2
(45) Date of Patent: May 30, 2023

(54) OCT SYSTEM, METHOD OF GENERATING OCT IMAGE AND STORAGE MEDIUM

(71) Applicant: KOH YOUNG TECHNOLOGY INC., Seoul (KR)

(72) Inventors: Young Joo Hong, Gwangmyeong-si (KR); Jeong Hun Choi, Bucheon-si (KR); Deok Hwa Hong, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 1005 days.

(21) Appl. No.: 16/416,513

(22) Filed: May 20, 2019

(65) Prior Publication Data

US 2019/0350459 A1    Nov. 21, 2019

(30) Foreign Application Priority Data

May 21, 2018   (KR) ........................ 10-2018-0057902

(51) Int. Cl.
  *A61B 5/00*    (2006.01)
  *G06T 5/00*    (2006.01)
  (Continued)

(52) U.S. Cl.
  CPC ............ *A61B 5/0066* (2013.01); *G06T 5/001* (2013.01); *G06T 5/50* (2013.01); *G06T 11/005* (2013.01);
  (Continued)

(58) Field of Classification Search
  CPC ..... A61B 5/0066; A61B 3/102; A61B 5/0073; G06T 5/001; G06T 5/50; G06T 11/005;
  (Continued)

(56) References Cited

U.S. PATENT DOCUMENTS

| 2007/0103693 A1 | 5/2007 | Everett et al. |
| 2008/0192236 A1 | 8/2008 | Smith et al. |

(Continued)

FOREIGN PATENT DOCUMENTS

| CN | 101115436 | 1/2008 |
| CN | 101949689 | 1/2011 |

(Continued)

OTHER PUBLICATIONS

Donglin et al., "Correction of image distortions in endoscopic optical coherence tomography based on two-axis scanning MEMS mirrors", Optical Society of Americ. published on 2013 (Year: 2013).*

(Continued)

*Primary Examiner* — Mekonen T Bekele
(74) *Attorney, Agent, or Firm* — Kile Park Reed & Houtteman PLLC

(57) ABSTRACT

The present disclosure relates to a method of correcting a three-dimensional image. To correct an image distorted by coherence gate curvature (CGC) occurring by an optical system, the method generates a three-dimensional image of a sample holder on which an object to be measured is placed from an interference signal, generates a CGC profile on the basis of an image of a cover glass of the sample holder appearing in the three-dimensional image, generates a CGC fitting curve from the CGC profile, and corrects the interference signal by using the CGC fitting curve. The present disclosure also relates to an OCT system capable of performing a method of correcting a three-dimensional image.

12 Claims, 8 Drawing Sheets

(51) Int. Cl.
  *G06T 5/50*    (2006.01)
  *G06T 11/00*   (2006.01)
(52) U.S. Cl.
  CPC .............. *G06T 2207/10101* (2013.01); *G06T 2207/20224* (2013.01)
(58) Field of Classification Search
  CPC ........... G06T 2207/10101; G06T 2207/20224; G01B 9/02064; G01B 9/02091; G01B 9/02072; G01B 11/2441; G02B 26/10
  See application file for complete search history.

(56) References Cited

U.S. PATENT DOCUMENTS

| | | | |
|---|---|---|---|
| 2010/0067020 | A1 | 3/2010 | Podoleanu |
| 2011/0032533 | A1 | 2/2011 | Izatt et al. |
| 2012/0188510 | A1 | 7/2012 | Suehira et al. |
| 2012/0256909 | A1* | 10/2012 | Ihara ................... H04N 13/117 345/419 |
| 2014/0253542 | A1* | 9/2014 | Jung ........................ G06T 3/40 345/419 |
| 2014/0268048 | A1 | 9/2014 | Iwase |
| 2017/0167846 | A1 | 6/2017 | Robledo et al. |
| 2018/0344163 | A1 | 12/2018 | Lee et al. |
| 2019/0271533 | A1 | 9/2019 | Robledo et al. |

FOREIGN PATENT DOCUMENTS

| | | |
|---|---|---|
| CN | 102599882 | 7/2012 |
| JP | 2009-507537 | 2/2009 |
| JP | 2012-147976 | 8/2012 |
| JP | 2014-176566 | 9/2014 |
| JP | 2017-116540 | 6/2017 |
| KR | 10-2014-0058159 | 5/2014 |
| KR | 10-2014-0060383 | 5/2014 |
| KR | 10-2017-0051194 | 5/2017 |
| WO | 2007/028531 | 3/2007 |
| WO | 2017/075089 | 5/2017 |

OTHER PUBLICATIONS

San der Jeught et al. "Large-Volume Optical Coherence Tomography With Real-Time Correction of Geometric Distortion Artifacts", measurement Science and Technology published on Mar. 2013. (Year: 2013).*
Japanese Office Action with English translation for Japanese Patent Application No. 2020-185397, dated Sep. 21, 2021.
Chinese Office Action, with English translation, corresponding to Chinese Application No. or Publication No. 201910423460.8, dated Sep. 28, 2020.
Sam Van der Jeught et al., "Real-time correction of geometric distortion artefacts in large-volume optical coherence tomography"; Measurement Science and Technology, vol. 24; No. 5., Mar. 21, 2013; pp. 1-5.
Donglin Wang et al., "Correction of image distortions in endoscopic optical coherence tomography based on two-axis scanning MEMS mirrors"; Biomedical Optics Express, vol. 4, No. 10; Oct. 1, 2013.
Jesus Diaz Diaz et al., "One step geometrical calibration method for optical coherence tomography"; Journal of Optics, vol. 18; No. 1, 015301; Dec. 1, 2015; pp. 1-10.
Volker Westphal et al., "Correction of geometric and refractive image distortions in optical coherence tomography applying Fermat's principle"; Optics Express, vol. 10, No. 9; May 2, 2002.
Extended European search report corresponding to European Patent Application No. 19175284.9, dated Sep. 3, 2019.
Benedikt W. Graf et al., "Correction of coherence gate curvature in high numerical aperture optical coherence imaging"; Optics Letters, vol. 35, No. 18; Sep. 15, 2010; pp. 3120-3122.
International Search report with English translation corresponding to International Application No. PCT/KR2019/006492, dated Sep. 9, 2019.
European Office Action corresponding to European Application No. 19 175 284.9 dated Jun. 8, 2021.
Japanese Office Action, with English translation, corresponding to Japanese Application No. 2019-094530, dated May 12, 2020.
Japanese Office Action with English translation for Japanese Patent Application No. 2020-185397, dated May 24, 2022.

* cited by examiner

FIG. 1

FIG. 7
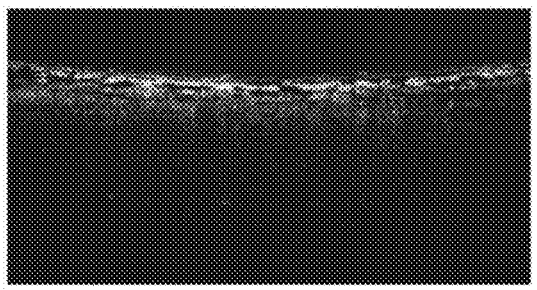
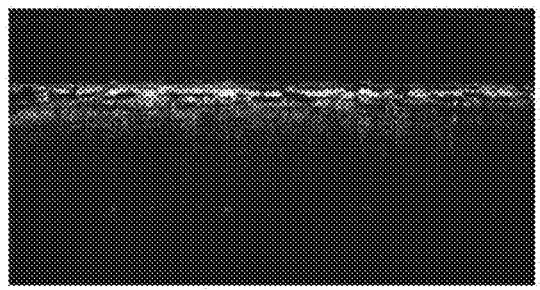
FIG. 8
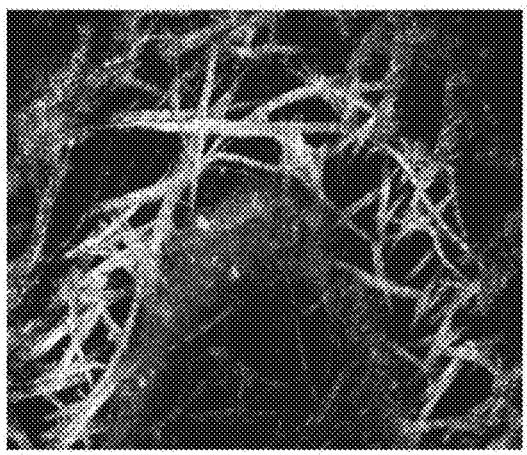
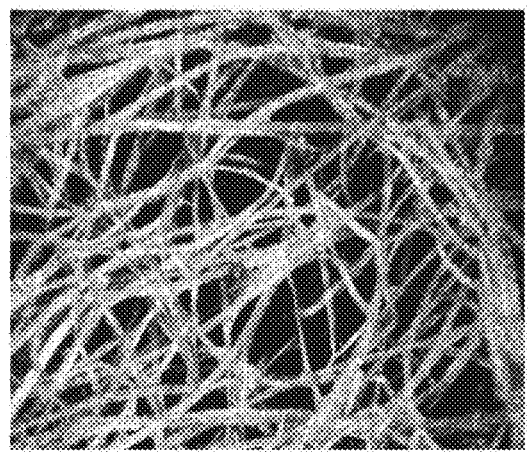

OCT SYSTEM, METHOD OF GENERATING OCT IMAGE AND STORAGE MEDIUM

CROSS-REFERENCE TO RELATED APPLICATION

This application is based upon and claims the benefit of priority from Korean Patent Application No. 10-2018-0057902, filed on May 21, 2018, the entire contents of which are incorporated herein by reference.

TECHNICAL FIELD

The present disclosure relates to an optical coherence tomography (OCT) system and a method of correcting a three-dimensional image in an OCT system.

BACKGROUND

A general optical coherence tomography (OCT) system generates a three-dimensional image of an object to be measured using reference light resulting from a laser beam reflected on a reference mirror and sample light backscattered by a sample to be measured. Specifically, OCT generates a three-dimensional image by analyzing an interference signal arising from the difference in optical path between the sample light and the reference light. A depth position at which the sample light having the same optical path length as the optical path length of the reference light is referred to as a zero delay, and a depth profile at the measurement point of the sample to be measured is represented by a position relative to the zero delay. A coherence gate refers to a three-dimensional range in which a cross-sectional image can be obtained due to the occurrence of interference with respect to the zero delay.

OCT provides three-dimensional structural information about a subsurface, which is difficult to identify only with two-dimensional images of a surface, by optically providing cross-sectional images without physical cutting. A depth range in which imaging is possible with OCT is determined on the basis of the wavelength of a laser beam used in OCT and the configuration of an optical system and is generally 2 to 3 mm. OCT has been diversely used in the diagnosis of ophthalmic diseases, such as a retina disease, an anterior segment disease, and an eyelid disease. In addition to ophthalmic diagnosis, the application of OCT has recently been extended to angiography, a blood flow test, and biopsy. Particularly, a microscope employing OCT, that is, an optical coherence microscope (OCM), has recently appeared, and there are growing demands for the generation of high-resolution three-dimensional images by using OCT.

A process of generating a three-dimensional image by using OCT includes an operation of scanning a measurement area of an object with laser beams in a transverse direction. To this end, the laser beams are reflected on a series of rotatable mirrors included in an optical system of an OCT system. The reflected laser beams pass through different positions from an optical axis on the optical system depending on the angle of reflection, and thus different points are measured by the laser beams. Here, although the laser beams are emitted from the same point that is a light source, optical paths through which the laser beams pass have different lengths depending on different measured points, which occur in the same manner as when light scattered on the sample to be measured returns. Thus, a depth position of the zero delay varies depending on a transverse position from the optical axis in an object space to be measured, and a three-dimensional coherence gate volume has a curved surface, such as a parabolic surface, perpendicular to the optical axis instead of having a rectangular parallelepiped shape. In OCT imaging, coherence gate curvature is a phenomenon by which, when a zero-delay position changes depending on transverse positions from an optical axis, a depth profile at the position appears to be individually moved.

SUMMARY

In a precedent study conducted by Benedikt W. Graf et al., there is proposed a method of correcting coherence gate curvature (CGC) of an optical coherence tomography (OCT) image of a sample to be measured by extracting an interference signal for a reference surface, analyzing a phase value according to a wave-number from the interference signal to calculate a CGC value, and correcting the phase of an interference signal used to measure the sample using this CGC value. (Benedikt W. Graf et al., "Correction of coherence gate curvature in high numerical aperture optical coherence imaging", Optics Letters 35 (18), 3120-3122, 2010). Using this method enables correction at a resolution higher than the resolution of a pixel in an image. However, the method using phase analysis proposed by Benedikt requires an excessive amount of calculations. In OCT imaging calculation, a Fourier transform is a high-load calculation, and Fourier transform calculation is generally needed once. However, to solve coherence gate curvature according to the Benedikt method, Fourier transform calculation is required three times.

An aspect of the present disclosure is to solve the foregoing problems of the related art and to correct distortion caused by CGC in generating a high-resolution three-dimensional image by using an OCT system.

Another aspect of the present disclosure is to correct distortion caused by CGC using a smaller amount of calculations even at a sub-pixel level in generating a high-resolution three-dimensional image by using an OCT system.

According to one embodiment of the present disclosure, an image correction method performed by an OCT system includes: obtaining an interference signal for a reference surface; generating a first image including a three-dimensional image of the reference surface from the interference signal for the reference surface; extracting a coherence gate curvature (CGC) profile from the first image; and generating a CGC fitting curve from the CGC profile.

According to another embodiment of the present disclosure, the image correction method performed by the OCT system further includes: obtaining an interference signal for a sample; correcting the interference signal for the sample by using the CGC fitting curve; and generating a second image from the corrected interference signal for the sample.

According to another embodiment of the present disclosure, in the image correction method performed by the OCT system, the extracting the CGC profile includes: selecting a first pixel set from pixels on an x-y plane of the three-dimensional image; and extracting, for the first pixel set, differences in relative depth position between a peak point in the three-dimensional image of the reference surface and points other than the peak point in the three-dimensional image of the reference surface.

According to another embodiment of the present disclosure, in the image correction method performed by the OCT system, the selecting the first pixel set includes selecting only a part of the pixels on the x-y plane of the three-dimensional image as the first pixel set.

According to another embodiment of the present disclosure, in the image correction method performed by the OCT system, the selecting the first pixel set includes selecting a part of the pixels on the x-y plane of the three-dimensional image as the first pixel set, based on strength of the interference signal corresponding to each pixel.

According to one embodiment of the present disclosure, an OCT system includes: an interferometer; a photodetector; a processor; and a storage unit, wherein the interferometer includes a light source, a beam splitter, and a reference mirror, the photodetector is configured to receive interference light that is generated by reference light and reflected light, the reference light being generated by a laser beam from the light source being reflected on the reference mirror, the reflected light being generated by the laser beam reflected on a reference surface, and to convert the interference light into an interference signal, and the processor is configured to obtain an interference signal for the reference surface, generate a first image including a three-dimensional image of the reference surface from the interference signal, extract a CGC profile from the first image, and generate a CGC fitting curve from the CGC profile.

According to another embodiment of the present disclosure, in the OCT system, the processor is configured to obtain an interference signal for a sample, correct the interference signal for the sample by using the CGC fitting curve, and generate a second image from the corrected interference signal for the sample.

According to another embodiment of the present disclosure, in the OCT system, when extracting the CGC profile, the processor is configured to, when extracting the CGC profile, select a first pixel set from pixels on an x-y plane of the three-dimensional image and extract, for the first pixel set, differences in relative depth position between a peak point in the three-dimensional image of the reference surface and points other than the peak point in the three-dimensional image of the reference surface.

According to another embodiment of the present disclosure, in the OCT system, when selecting the first pixel set, the processor is configured to select only a part of the pixels on the x-y plane of the three-dimensional image as the first pixel set.

According to another embodiment of the present disclosure, in the OCT system, when selecting the first pixel set, the processor is configured to select a part of the pixels on the x-y plane of the three-dimensional image as the first pixel set, based on strength of the interference signal corresponding to each pixel.

According to one embodiment of the present disclosure, a computer-readable medium is a computer-readable storage medium that stores program instructions executable by a processor, wherein the program instructions are configured to perform a method when executed by the processor, and the method includes: obtaining an interference signal for a reference surface; generating a first image including a three-dimensional image of the reference surface from the interference signal for the reference surface; extracting a CGC profile from the first image; generating a CGC fitting curve from the CGC profile; and generating a corrected interference signal by correcting the interference signal using the CGC fitting curve.

According to another embodiment of the present disclosure, in the computer-readable medium, the method further includes: obtaining an interference signal for a sample; correcting the interference signal for the sample using the CGC fitting curve; and generating a second image from the corrected interference signal for the sample.

According to another embodiment of the present disclosure, in the computer-readable medium, the extracting of the CGC profile includes: selecting a first pixel set from pixels on an x-y plane of the three-dimensional image; and extracting, for the first pixel set, differences in relative depth position between a peak point in the three-dimensional image of the reference surface and points other than the peak point in the three-dimensional image of the reference surface.

According to another embodiment of the present disclosure, in the computer-readable medium, the selecting the first pixel set includes selecting only a part of the pixels on the x-y plane of the three-dimensional image as the first pixel set.

According to another embodiment of the present disclosure, in the computer-readable medium, the selecting the first pixel set includes selecting a part of the pixels on the x-y plane of the three-dimensional image as the first pixel set, based on strength of the interference signal corresponding to each pixel.

BRIEF DESCRIPTION OF DRAWINGS

The accompanying drawings, which are incorporated in and constitute a part of the specification, illustrate embodiments of the present disclosure, and together with the general description given above and the detailed description of the embodiments given below, serve to explain the principles of the present disclosure.

FIG. 1 illustrates a principle by which CGC occurs.

FIGS. 7 and 8 illustrate a comparison of an image distorted by CGC with a corrected image thereof.

DETAILED DESCRIPTION

Figure 2:
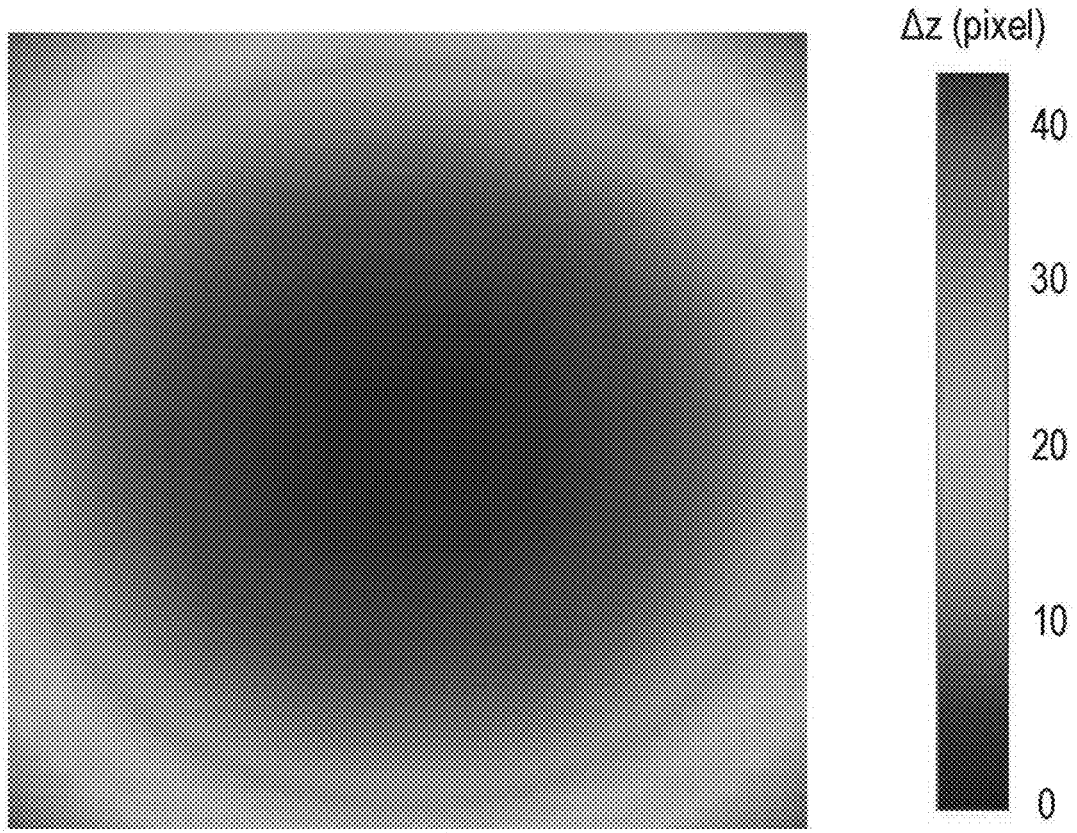
FIG. 2 illustrates an example of CGC.

Embodiments of the present disclosure are illustrated for describing the present disclosure. Embodiments of the present disclosure may be implemented in various forms, and the present disclosure is not construed as being limited to the embodiments illustrated below or to the detailed descriptions of these embodiments.

The term "unit" used in these embodiments means a software component or a hardware component, such as a field-programmable gate array (FPGA) and an application-specific integrated circuit (ASIC). However, a "unit" is not limited to software and hardware but may be configured to be an addressable storage medium or may be configured to run on one or more processors. For example, a "unit" includes components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "units" may be combined into a smaller number of components and "units" or may be further subdivided into additional components and "units."

All technical or scientific terms used herein have meanings that are generally understood by a person having ordinary knowledge in the art to which the present disclosure pertains, unless otherwise specified. The terms used herein are selected only for a more clear illustration of the present disclosure, and are not intended to limit the scope of claims in accordance with the present disclosure.

A singular expression used herein can include meanings of plurality, unless otherwise mentioned, and the same is applicable to a singular expression stated in the claims.

The terms "first", "second", etc. used herein are used to identify a plurality of components from one another, and are not intended to limit the order or importance of the relevant components.

The expressions "include", "provided with", "have" and the like used herein should be understood as open-ended terms connoting the possibility of inclusion of other embodiments, unless otherwise mentioned in a phrase or sentence including the expressions.

The expressions "based on" and "on the basis of" used herein are used to describe one or more factors that influence a decision, an action of judgment, or an operation described in a phrase or sentence including the relevant expression, and this expression does not exclude additional factors influencing the decision, the action of judgment or the operation.

When a certain component is described as "coupled to" or "connected to" another component, this should be understood as having a meaning that the certain component may be coupled or connected directly to the other component or that the certain component may be coupled or connected to the other component via a new intervening component.

It should be understood that the terms "optical coherence tomography (OCT) image," "OCT picture," or "three-dimensional OCT image" used herein refer to a three-dimensional image generated using OCT unless specified otherwise. Further, it should be understood that the term "OCT measurement" used herein refers to a process of obtaining an interference signal by applying OCT to an object of which a three-dimensional image is to be generated using OCT, and generating a three-dimensional image from the interference signal unless specified otherwise.

An OCT system may obtain depth profile information about an object to be measured from an interference signal generated by reference light resulting from a laser beam reflected on a reference mirror and sample light resulting from the same laser beam backscattered by the object to be measured and may scan the object with laser beams two-dimensionally in a transverse direction, thereby generating a three-dimensional image. Scanning a measurement area may be performed in a manner such that an interference signal is obtained by scanning the measurement area with a laser in a first direction and then an interference signal is obtained by repeating first-direction scanning in a second direction perpendicular to the first direction. The OCT system may process the obtained interference signals, thereby generating a three-dimensional image of the object to be measured.

Here, the first direction may be referred to as a default scan direction or a fast axis direction, and the second direction may be referred to as a subsidiary scan direction or a slow axis direction. Alternatively, the first direction may be referred to as an x-axis direction, and the second direction may be referred to as a y-axis direction. A scanning method of changing a measurement point used by the OCT system is not limited to the foregoing raster mode, and known scanning methods that the OCT system can implement may be used.

In order to adjust a measurement point, an optical system including a series of rotatable mirrors may adjust the traveling path of a laser beam. Accordingly, a transverse position at which a laser beam forms an image in the space of an object to be measured may be adjusted. Laser beams pass through different traveling paths depending on the transverse position of the object to be measured, and the lengths of optical paths may vary depending on the transverse position. As described above, differences in optical path length may cause coherence gate distortion. Particularly, an OCM may include a high-magnification lens in an optical system in order to obtain a high-resolution image, and using the high-magnification lens may further increase differences in optical path length depending on a transverse distance from an optical axis and may worsen coherence gate curvature (CGC), thus aggravating the distortion of an OCT image.

Figure 1:
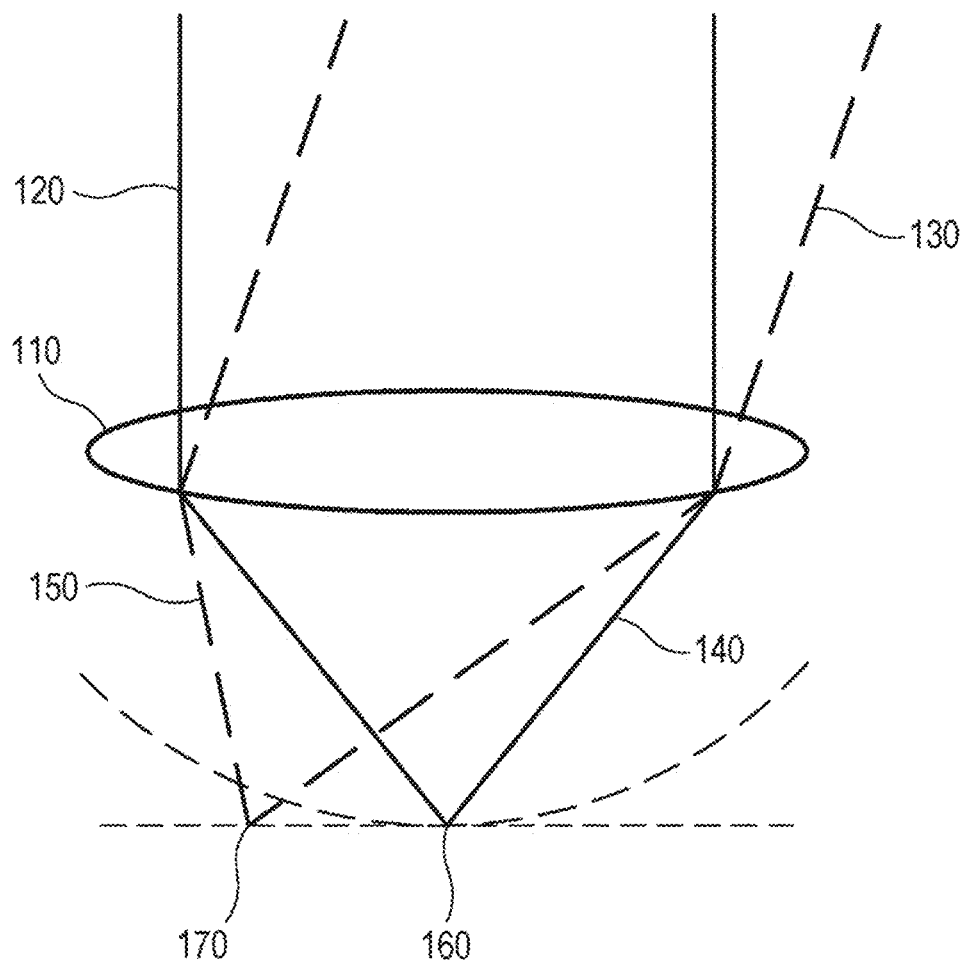
Figure 3:
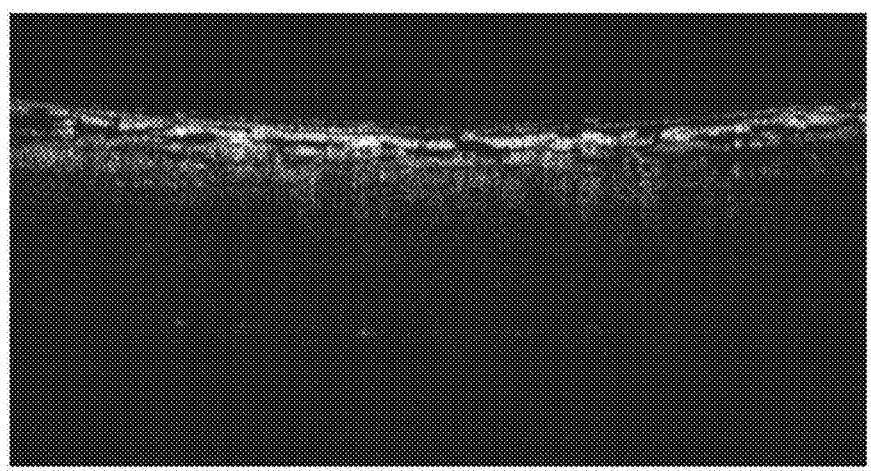
FIG. 3 illustrates an example in which an image is distorted by CGC.

FIG. 1 illustrates a principle by which CGC occurs according to the foregoing description. Referring to FIG. 1, the traveling path of laser beams 120 and 130 varies depending on points 160 and 170 scanned by the laser beams 120 and 130 passing through a lens 110, and accordingly optical path lengths 140 and 150 are different. The distribution of optical path differences may be in proportion to the distance from the center of a scan area, the central axis of an optical system, or the center of the lens and may have, for example, a radial form as shown in FIG. 2. FIG. 3 illustrates an example in which an image is actually distorted by CGC. Referring to FIG. 3 illustrating a vertical cross-sectional view of an image generated by applying OCT to a flat surface, although the surface to be measured is flat, the surface to be measured is shown to curve downwards in the actual image, which results from the distortion of the image by CGC. Aspects of distortion by CGC may change depending on the configuration of an optical system. As described above, when obtaining a high-resolution three-dimensional image, the difference between optical paths to scan points becomes larger as laser beams pass through a lens, thus resulting in a greater difference between an actual structure and an image.

To solve the above problems, the present disclosure provides a method for generating a three-dimensional image of an object to be measured through an OCT system and generating a three-dimensional image by correcting the distortion of an image by CGC and the operation of an OCT system performing the same, which will be described hereinafter with reference to the accompanying drawings. Like reference numerals are used to indicate like elements in the drawings, and redundant descriptions of like elements are omitted herein.

Figure 4:
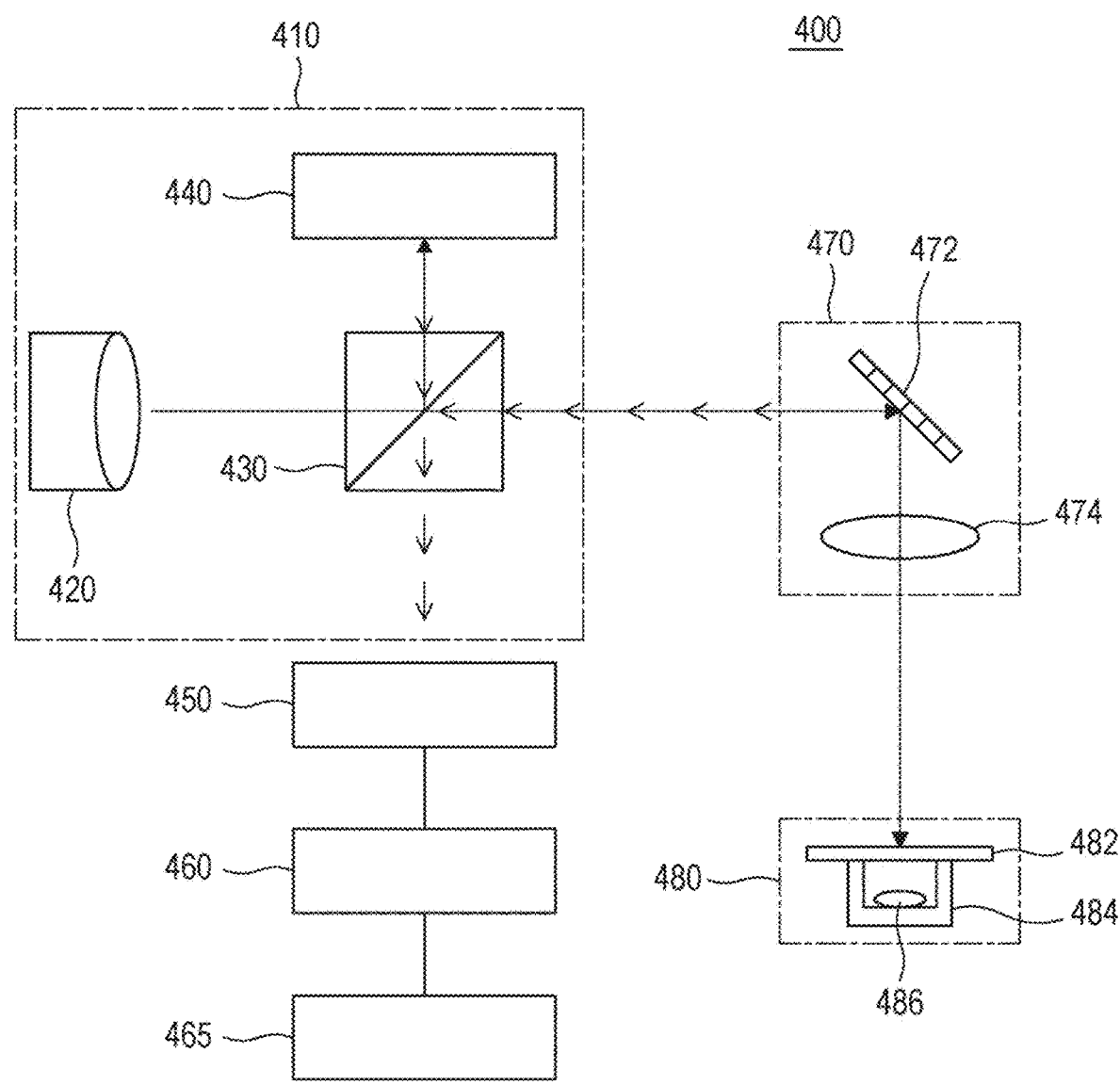
FIG. 4 is a block diagram illustrating an OCT measurement system according to one embodiment of the present disclosure.

FIG. 4 illustrates an OCT system 400 according to the present disclosure. The OCT system 400 of FIG. 4 may include an interferometer 410 to obtain an interference signal from a sample as an object to be measured using OCT, a photodetector 450 to receive interference light from the interferometer 410, to generate a signal, and to process the generated signal, a processor 460, and a storage unit 465. The interferometer 410 may include a light source 420, a beam splitter 430, and a reference mirror 440. A sample to be measured of which an OCT image is to be generated by the OCT system 400 may be disposed in a sample holder 480. Although omitted for the convenience of illustration, components of the OCT system 400 may be connected to each other through wired communication line or wireless communication technology capable of transmitting signals, such as optical cable, optical fiber, and coaxial cable. The configuration of the system illustrated in FIG. 4 is merely an example, and it would be clearly understood by those skilled in the art that a component may be changed or added as needed without departing from the idea of the present disclosure and that such change or addition may also be included in the scope of the present disclosure.

The light source 420 emits a laser beam to be used for OCT measurement. A tunable laser may be used for the light source 420. Some portions of the laser beams emitted from the light source 420 may be refracted by the beam splitter 430 and may be reflected on the reference mirror 440, thereby forming the reference light. Other portions of the laser beam emitted from the light source 420 may pass through the beam splitter 430 and may be reflected on the sample holder 480, thereby forming sample light.

The beam splitter 430 may refract some portions of the laser beams emitted from the light source 420 to be emitted to the reference mirror 440. The beam splitter 430 may pass the reference light reflected on the reference mirror 440 to head to the photodetector 450. The beam splitter 430 may pass other portions of the laser beams emitted from the light source 420 to be emitted to the sample holder 480. The beam splitter 430 may refract the sample light reflected on the sample holder 480 to head to the photodetector 450.

The photodetector 450 may convert interference light, generated from the reflected light and the sample light, into an interference signal and may transmit the interference signal to the processor 460. The processor 460 may generate a three-dimensional image of the object to be measured from the transmitted interference signal. The processor 460 may further process the three-dimensional image to generate correction information for correcting CGC. The processor 460 may correct the interference signal on the basis of the generated correction information. The processor 460 may generate a corrected three-dimensional image on the basis of the corrected interference signal. A detailed process by which the processor 460 generates the corrected three-dimensional image will be described later.

The OCT system 400 may include the storage unit 465 connected to communicate with the photodetector 450 and/or the processor 460 if necessary. The storage unit 465 may receive an interference signal from the photodetector 450 and may store the interference signal. The storage unit 465 may transmit the stored interference signal to the processor 460 so that the processor 460 can generate a three-dimensional image. The storage unit 465 may store all information including instructions, which are necessary for the processor 460 to process an interference signal, to generate the three-dimensional image, and to correct the three-dimensional image. The storage unit 465 may be integrated with the processor 460 or may be included as a part of the processor 460.

The sample holder 480 may include a holder 484 in which the sample 486 is disposed and a cover glass 482 covering the holder 484.

The system 400 of FIG. 4 includes an optical system 470. The optical system 470 includes a mirror array 472 for adjusting a destination of a laser beam and a lens 474 for obtaining a high-resolution image. As described above, the optical system 470 may be disposed between the beam splitter 430 and the sample holder 480 in order to generate a high-resolution image in using OCT. As described above, as the reflection direction of the laser beam is changed by the mirror array 472, an angle at which the laser beam enters the lens 474 is slightly changed, and differences in the angle of the laser beam entering the lens changes the length of an optical path for each transverse position of a scan point, thus causing a phenomenon that a coherence gate has a curved surface, that is, CGC phenomenon. Here, the optical system 470 illustrated in FIG. 4 is merely a simplified example of an optical system including a mirror and a lens to generate a high-resolution image. It would be clearly understood by those skilled in the art that a specific configuration of the optical system 470 may be diversified according to methods for generating a high-resolution image. A device and a method according to the present disclosure can correct the distortion of an image due to CGC occurring by an optical system and can provide an accurate three-dimensional image.

An OCT system according to the present invention may identify characteristics of CGC incurred by an optical system included in the OCT system and generate information for correction on the basis of the characteristics before performing OCT measurement on a sample as an object to be actually measured and generating a three-dimensional image. Specifically, the OCT system may generate a three-dimensional image of a certain reference surface and may generate information for correction from the three-dimensional image. When the OCT system according to the present disclosure generates the information for correction, the OCT system may extract a series of points corresponding to the reference surface from the three-dimensional image and may generate a fitting curve representing the shape of CGC on the basis of the points. The generated fitting curve may be used subsequently as information for correction. After the information for correction is generated, the OCT system may dispose the sample as the object to be actually measured in the sample holder and may perform OCT measurement thereon, thereby generating a three-dimensional image of the sample. While performing three-dimensional measurement on the sample, the OCT system may correct an interference signal obtained during OCT measurement of the sample by using the existing generated information for correction. The OCT system may generate a three-dimensional image from the corrected interference signal, thereby generating a corrected three-dimensional image from which CGC is removed.

Figure 5:
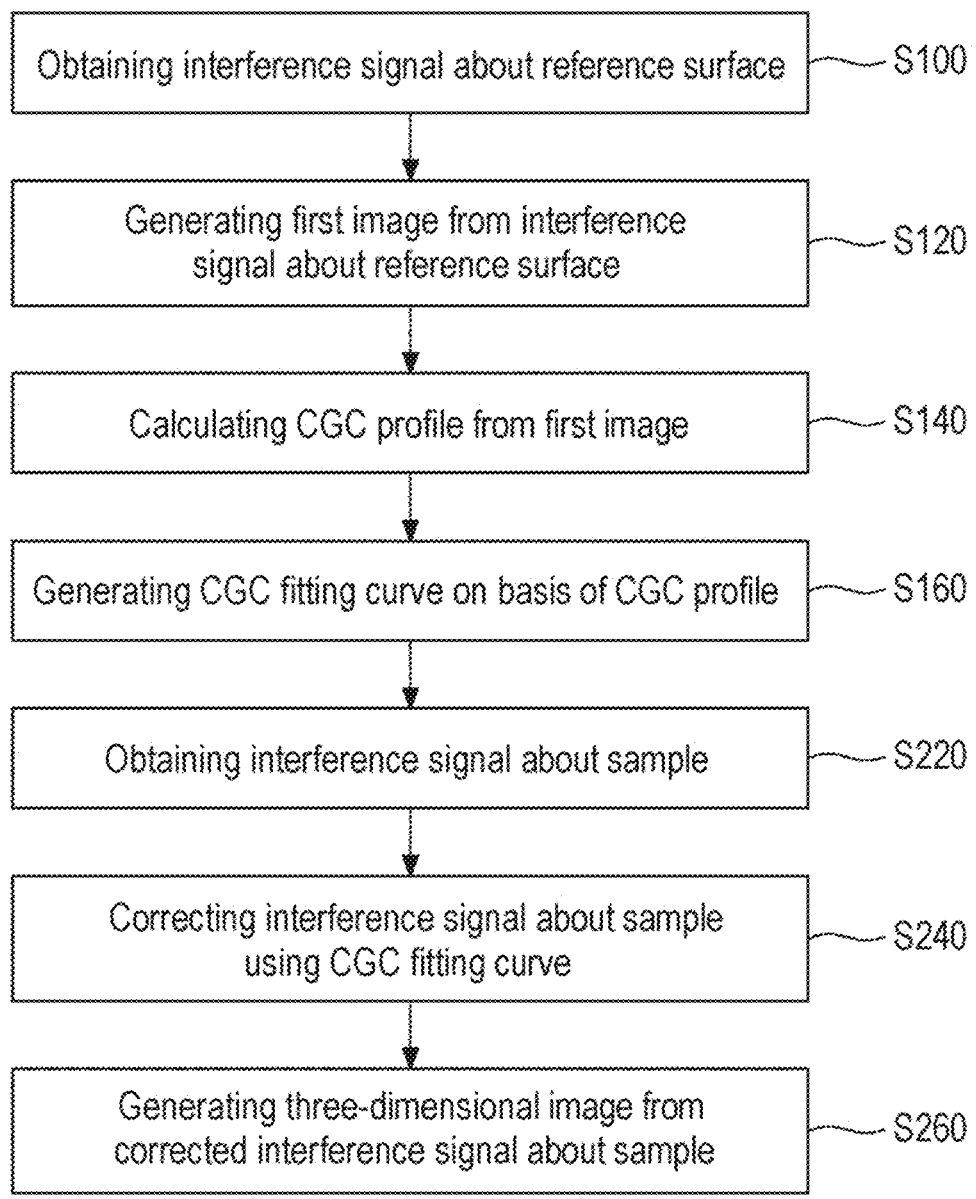
FIG. 5 is a flowchart illustrating a method of correcting a three-dimensional image according to one embodiment of the present disclosure.

FIG. 5 is a flowchart illustrating a CGC correction method 500 according to the present disclosure. The CGC correction method 500 according to the present disclosure may be performed by the OCT system 400 illustrated in FIG. 4. Specifically, the CGC correction method 500 may be performed by the processor 460 included in the OCT system 400.

In step S100, the OCT system may obtain an interference signal about a reference surface. The reference surface may be the cover glass of the sample holder. Further, the reference surface may be a plane of which a three-dimensional image can be obtained by OCT. The process of obtaining the interference signal about the reference surface may be performed by the OCT system 400 of the present disclosure, and a specific method thereof is the same as that described above and thus will not be repeatedly explained.

In step S120, the OCT system may generate a first image from the interference signal. The first image may be a three-dimensional image generated from the interference signal. The first image may include a three-dimensional image about the reference surface. Here, the first image may include an image of the reference surface distorted due to CGC incurred by the current configuration of the OCT system.

In step S140, the OCT system may calculate a CGC profile. The CGC profile may include the size of CGC incurred at each position on x-y plane pixels included in the three-dimensional image. Here, the size of CGC may indicate the difference between z-axis values that occur by CGC. Specifically, the reference surface, which is supposed to be seen as flat, may actually have a curved-surface shape due to CGC in the three-dimensional image measured by OCT, and accordingly the difference in z-axis depth between a point supposed to be actually seen as a flat surface and a point seen in the image may be determined as the size of CGC. The accuracy of the CGC profile depends on the resolution of pixels in a depth direction. When CGC is corrected using the CGC profile as it is, an x-z cross section is corrected as the cross section of a Fresnel lens, and thus a defective pattern of contours may additionally occur in an x-y direction.

Figure 6:
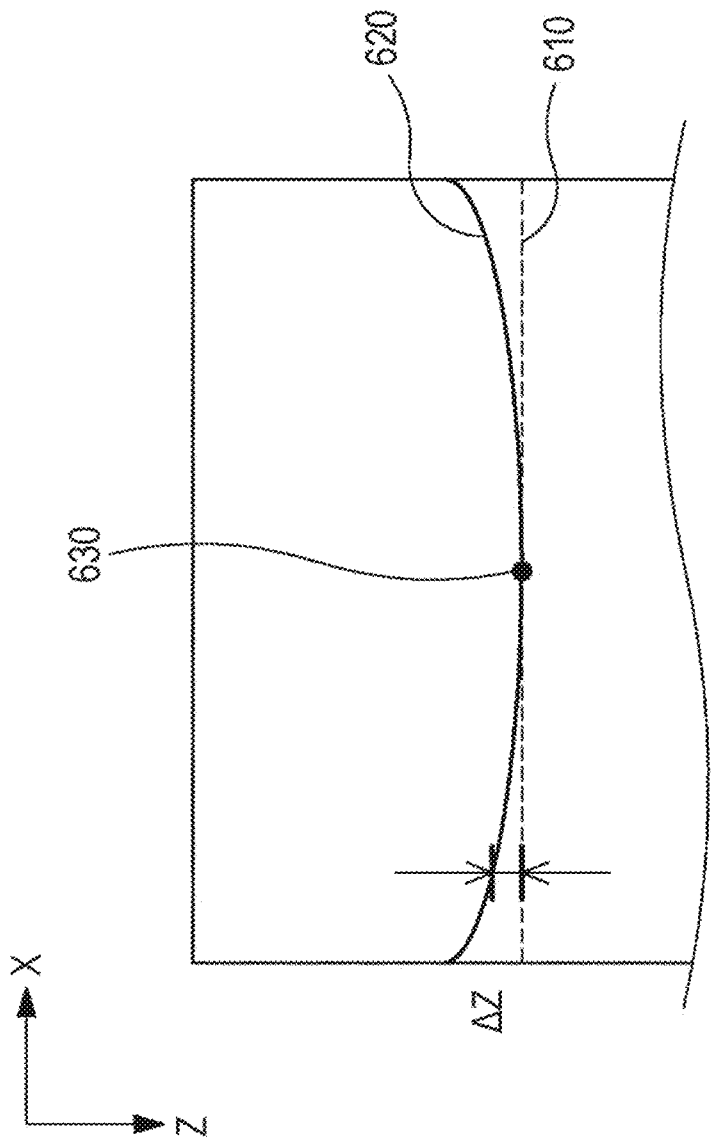
FIG. 6 illustrates a method of generating a CGC profile in the method of correcting the three-dimensional image according to the present disclosure.

FIG. 6 illustrates a method of determining the size of CGC and a CGC profile. FIG. 6 shows an x-z plane on which an OCT image is formed, which includes a distorted image of a reference surface 620. The reference surface is supposed to be actually seen as having a constant thickness in the image but is indicated by a single line in this specification for the convenience of description. Here, the reference surface actually has a flat shape and thus is supposed to be seen as a flat surface 610 in the image. However, unlike the actual shape, the reference surface is seen to have a distorted shape 620 in the image due to CGC. The size of CGC indicates the difference between z-axis values in the image. Specifically, the difference $\Delta z$ in depth between the peak point 630 in the distorted image of the reference surface and other points of the reference surface is defined as a CGC size. Although a description of FIG. 6 is made with reference to the x-z plane at a particular y position for the convenience of description, it would be understood by those skilled in the art that the size of CGC can be measured at any point on the x-y plane.

In step S160, the OCT system may generate a CGC fitting curve. The CGC fitting curve may be represented by an equation showing the form of CGC appearing on the first image. The CGC fitting curve may be generated on the basis of the CGC profile obtained in step S140. In the CGC correction method according to one embodiment of the present disclosure, CGC correction is performed by using the CGC fitting curve instead of directly using the CGC profile for correction, making it possible to obtain continuous CGC information with an accuracy corresponding to a sub-pixel resolution level from the CGC profile with an accuracy corresponding to a pixel resolution level. Specifically, as described above in FIG. 6, the CGC fitting curve may be generated on the basis of the value of $\Delta z$ at each point in an x direction and a y direction on the first image of the sample. When generating the CGC fitting curve, a known graph fitting method may be used. The CGC fitting curve may be a quadratic function in (x, y) represented by Equation 1.

$$Z_{mirror}(x,y)=ax^2+by^2cxy+dx+ey+f \quad \text{(Equation 1)}$$

When the CGC fitting curve is generated, the OCT system may correct the interference signal by using the CGC fitting curve. The interference signal may be corrected by Equation 2.

$$S_c(x,y,k)=S(x,y,k)X \exp\{-i\cdot Z_{mirror}(x,y)\cdot k\} \quad \text{(Equation 2)}$$

In Equation 2, $S_c$ may denote a corrected interference signal, S may denote the interference signal, $Z_{mirror}$ may denote the obtained CGC fitting curve, and k may denote the wave number of a laser.

After the interference signal is corrected as described above, a three-dimensional image is generated from the corrected interference signal, thereby finally obtaining a three-dimensional image in which distortion due to CGC is corrected. In one embodiment, a left picture of FIG. 7 is an x-z plane image of the reference surface including distortion due to CGC, in which the reference surface is supposed to be flat but is seen to be curved downwards. When the interference signal is corrected according to the above method and a three-dimensional image is generated from the corrected interference signal, the reference surface may be corrected to be flat as in a right image of FIG. 7.

Similarly, after generating information for correction by performing OCT measurement on the reference surface, the OCT system may correct an OCT image of an object to be actually measured. In one embodiment, in step S220, the OCT system may obtain an interference signal of the sample in order to perform OCT measurement on the sample of which a three-dimensional image is to be actually generated. In step S240, the OCT system may correct the interference signal of the sample on the basis of the CGC fitting curve generated in step S160. Finally, in step S260, the OCT system may generate a three-dimensional image from the corrected interference signal. The generated image is an image in which distortion due to CGC is corrected. FIG. 8 illustrates the three-dimensional image of the sample with distortion corrected, which is seen from a z-axis direction. A depth-direction portion is not accurately measured by a conventional method as in a left image but is clearly observed in the image due to the correction of distortion as in a right image.

The CGC correction method according to the embodiment of the present disclosure may generate a CGC profile with an accuracy corresponding to a pixel resolution from a finally used OCT image in a first stage and may fit the CGC profile into a function model to thereby analytically obtain final CGC information, making it possible to correct CGC distortion with a sub-pixel accuracy. In order to perform CGC correction at a sub-pixel level according to a conventional method, a phase value is first analyzed from an interference signal, and CGC is calculated from the phase value and is used for correction, in which case a large amount of calculation is required. The CGC correction method according to the embodiment of the present disclosure enables correction of distortion due to CGC at a sub-pixel level while considerably reducing the amount of calculation. Further, since the amount of calculation is reduced, it is possible to significantly increase a processing speed for correcting CGC distortion.

According to another embodiment of the present disclosure, it is possible to perform more accurate correction while further reducing the amount of calculation for performing CGC correction. Hereinafter, a CGC correction method according to another embodiment of the present disclosure will be described.

In the foregoing method, a CGC equation is generated through fitting on the basis of pixels shown in an image.

However, in the CGC correction method according to the other embodiment of the present disclosure, only a part of pixels shown in an image may be used via sampling instead of using all the pixels.

Figure 9:
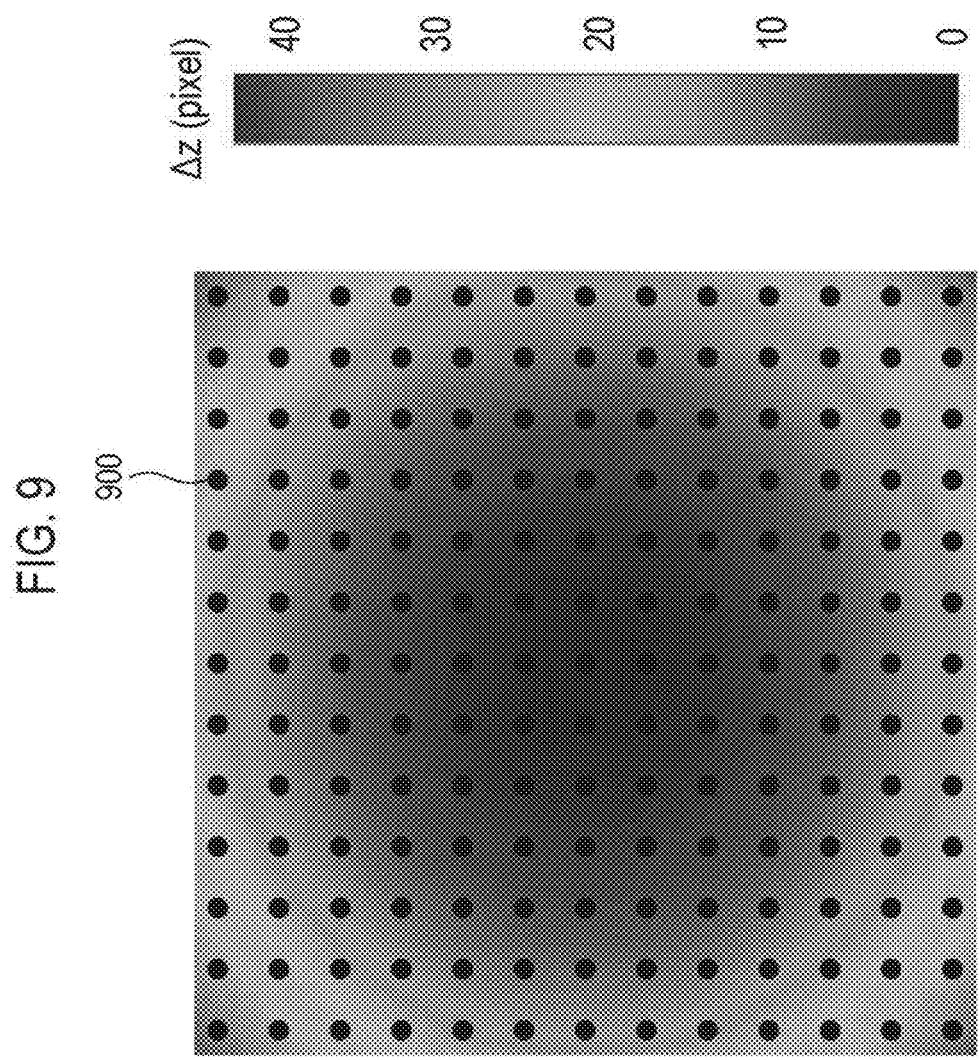
FIG. 9 illustrates a method of correcting a three-dimensional image according to another embodiment of the present disclosure.

In one embodiment, when an image generated from an interference signal is an image of 1000×1000 pixels in width and length, it is necessary to perform a process of generating a CGC profile for a total of 1,000,000 pixels by applying values from 1 to 1000 to x and y in Equation 1. FIG. 9 illustrates sample pixels equally selected in the x direction and the y direction. When CGC information is obtained not about all x- and y-direction pixels in an image but only about a part of sampled pixels, it is possible to significantly reduce the total amount of calculations. In the above example, when sampling is performed on 100 coordinates in each of the x direction and the y direction, CGC profiles only for a total of 10,000 pixels are generated and are applied to Equation 1, thereby generating a CGC fitting curve and correcting an interference signal while reducing the amount of calculations to 1/100. As described above, after a part of pixels are sampled, correction information about the sampled pixels are generated and used to correct an interference signal, thereby significantly reducing the amount of calculations necessary to correct CGC distortion.

Further, in the CGC correction method according to the other embodiment of the present disclosure, when selecting a sample for generating a CGC correction parameter, a sample may be selected on the basis of the strength of a signal from the reference surface. The difference in optical path, which causes CGC to occur, tends to increase as the distance between an optical axis, which is the center of a laser beam, and a point at which the laser is actually reflected, increases. Thus, when OCT measurement is performed, the strength of a signal from the reference surface is not uniformly distributed on the x-y plane but may have a shape similar to a concentric circle centralized by the optical axis. Alternatively, the distribution of signal strength may have a different shape depending on the configuration of an optical system that emits a laser beam to an object to be measured. As such, the differences in the strength of an interference signal may be used to select a sample needed to generate a CGC profile.

Figure 10:
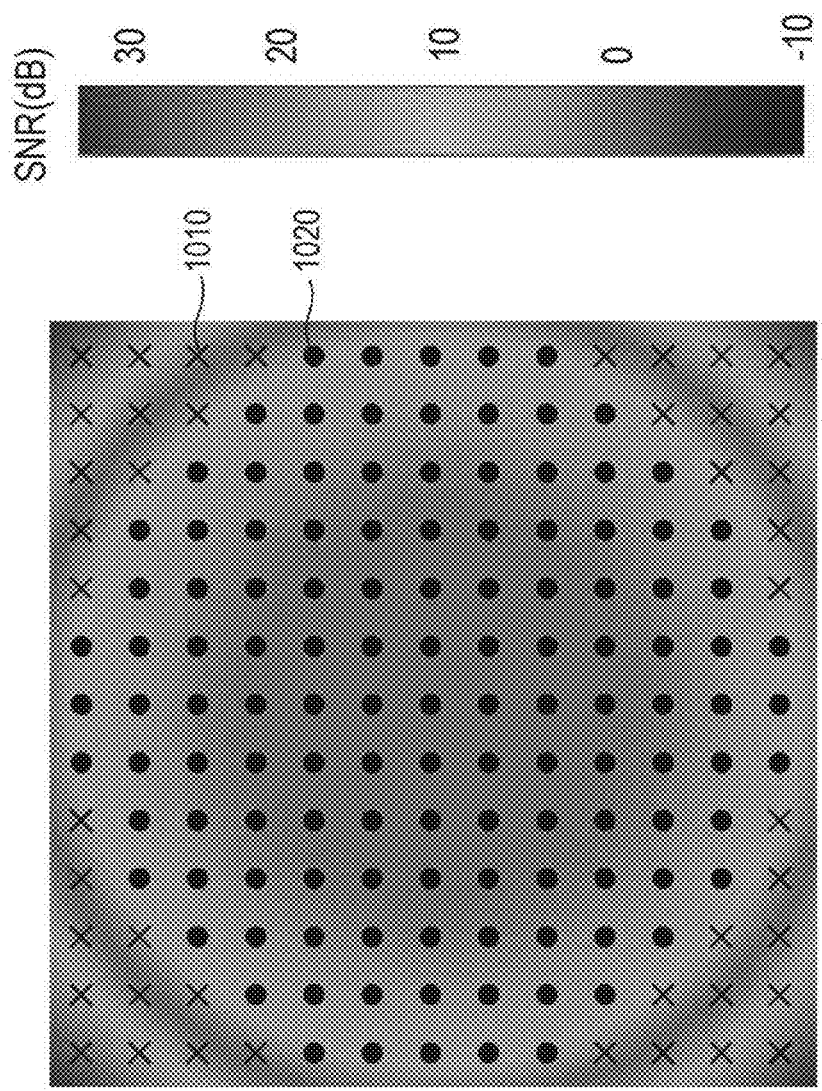
FIG. 10 illustrates a method of correcting a three-dimensional image according to yet another embodiment of the present disclosure.

FIG. 10 illustrates the strength of an interference signal obtained by an OCT system including an optical system, such as a lens, on an x-y plane. Here, signal strength in pixels 1010 located far from the optical axis of a laser beam is weaker than that in pixels 1020 located close to the optical axis. Thus, a CGC profile value measured at the pixels 1010 may be less reliable than a CGC profile value at the pixels 1020. Accordingly, when selecting a pixel for generating a CGC profile, instead of selecting samples evenly in the x-axis and y-axis directions as described above, samples may be selected in consideration of signal strength and a CGC profile may be generated on the basis of the selected samples. When a CGC fitting curve is generated on the basis of the CGC profile generated by this method and is used to correct an interference signal, it is possible to further reduce the amount of calculations than where samples are evenly selected. Further, since a CGC profile value having low reliability is excluded from the generation of a CGC fitting curve, if a pixel having a strong strength of an interference signal is further included as a sample, it is possible to perform more accurate CGC correction using the same amount of calculations than in the above embodiment.

According to one embodiment of the present disclosure, an OCT system can generate a three-dimensional image in which distortion due to a CGC phenomenon occurring by an optical system is corrected.

According to one embodiment of the present disclosure, an OCT system can correct and generate a three-dimensional image in which distortion due to a CGC phenomenon occurring by an optical system is corrected even with a smaller amount of calculation.

While the foregoing methods have been described with respect to particular embodiments, these methods may also be implemented as computer-readable codes on a computer-readable recording medium. The computer-readable recoding medium includes any kind of data storage devices that can be read by a computer system. Examples of the computer-readable recording medium includes ROM, RAM, CD-ROM, magnetic tape, floppy disk, optical data storage device and the like. Also, the computer-readable recoding medium can be distributed to the computer systems which are connected through a network so that the computer-readable codes can be stored and executed in a distributed manner. Further, functional programs, codes and code segments for implementing the foregoing embodiments can easily be inferred by programmers in the art to which the present disclosure pertains.

Although the present disclosure has been described with reference to some embodiments, it should be noted that various substitutions, modifications, and changes can be made without departing from the spirit and scope of the present disclosure which can be understood by those skilled in the art to which the present disclosure pertains. In addition, it should be noted that that such substitutions, modifications, and changes are intended to fall within the scope of the appended claims.

What is claimed is:

1. A method of generating an optical coherence tomography (OCT) image performed by an OCT system, the method comprising:
    obtaining an interference signal for a reference surface;
    generating a first image comprising a three-dimensional image of the reference surface from the interference signal for the reference surface;
    selecting a first pixel set from pixels on an x-y plane of the three-dimensional image based on strength of the interference signal corresponding to each pixel;
    extracting for the first pixel set, differences in relative depth position between a peak point in the three-dimensional image of the reference surface and points other than the peak point in the three-dimensional image of the reference surface;
    calculating a coherence gate curvature (CGC) profile by using the differences extracted for the first pixel set; and
    generating a CGC fitting curve from the CGC profile.

2. The method of claim 1, further comprising:
    obtaining an interference signal for a sample;
    correcting the interference signal for the sample by using the CGC fitting curve; and
    generating a second image from the corrected interference signal for the sample.

3. The method of claim 1, wherein the selecting the first pixel set comprises selecting only a part of the pixels on the x-y plane of the three-dimensional image as the first pixel set.

4. The method of claim 1, wherein the selecting the first pixel set comprises selecting a part of the pixels on the x-y plane of the three-dimensional image as the first pixel set, based on strength of the interference signal corresponding to each pixel.

5. An OCT system comprising:
an interferometer;
a photodetector;
a processor; and
a storage unit,
wherein the interferometer comprises a light source, a beam splitter, and a reference mirror,
wherein the photodetector is configured to:
  receive interference light that is generated by reference light and reflected light, the reference light being generated by a laser beam from the light source being reflected on the reference mirror, the reflected light being generated by the laser beam reflected on a reference surface; and
  convert the interference light into an interference signal, and
wherein the processor is configured to:
  obtain an interference signal for the reference surface;
  generate a first image comprising a three-dimensional image of the reference surface from the interference signal;
  select a first pixel set from pixels on an x-y plane of the three-dimensional image based on strength of the interference signal corresponding to each pixel;
  extract for the first pixel set, differences in relative depth position between a peak point in the three-dimensional image of the reference surface and points other than the peak point in the three-dimensional image of the reference surface;
  calculate a CGC profile by using the differences extracted for the first pixel set; and
  generate a CGC fitting curve from the CGC profile.

6. The OCT system of claim 5, wherein the processor is configured to:
  obtain an interference signal for a sample;
  correct the interference signal for the sample by using the CGC fitting curve; and
  generate a second image from the corrected interference signal for the sample.

7. The OCT system of claim 5, wherein the processor is configured to, when selecting the first pixel set, select only a part of the pixels on the x-y plane of the three-dimensional image as the first pixel set.

8. The OCT system of claim 5, wherein the processor is configured to, when selecting the first pixel set, select a part of the pixels on the x-y plane of the three-dimensional image as the first pixel set, based on strength of the interference signal corresponding to each pixel.

9. A computer-readable storage medium that stores program instructions executable by a processor, the program instructions being configured to perform a method when executed by the processor, the method comprising:
  obtaining an interference signal for a reference surface;
  generating a first image comprising a three-dimensional image of the reference surface from the interference signal;
  selecting a first pixel set from pixels on an x-y plane of the three-dimensional image based on strength of the interference signal corresponding to each pixel;
  extracting for the first pixel set, differences in relative depth position between a peak point in the three-dimensional image of the reference surface and points other than the peak point in the three-dimensional image of the reference surface;
  calculating extracting a CGC profile by using the differences extracted for the first pixel set;
  generating a CGC fitting curve from the CGC profile; and
  generating a corrected interference signal by correcting the interference signal by using the CGC fitting curve.

10. The computer-readable storage medium of claim 9, wherein the method further comprises:
  obtaining an interference signal for a sample;
  correcting the interference signal for the sample by using the CGC fitting curve; and
  generating a second image from the corrected interference signal for the sample.

11. The computer-readable storage medium of claim 9, wherein the selecting the first pixel set comprises selecting only a part of the pixels on the x-y plane of the three-dimensional image as the first pixel set.

12. The computer-readable storage medium of claim 9, wherein the selecting the first pixel set comprises selecting a part of the pixels on the x-y plane of the three-dimensional image as the first pixel set, based on strength of the interference signal corresponding to each pixel.

* * * * *